United States Patent
Akalin et al.

(10) Patent No.: US 6,401,058 B1
(45) Date of Patent: Jun. 4, 2002

(54) RECIPROCATING SYSTEM FOR SIMULATING FRICTION AND WEAR

(75) Inventors: Ozgen Akalin, Detroit; Golam M. Newaz, Ann Arbor, both of MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 09/249,019

(22) Filed: Feb. 12, 1999

(51) Int. Cl.$^7$ ............................ G01N 3/56; G05B 17/00
(52) U.S. Cl. ...................... 703/7; 702/34; 73/7; 73/9
(58) Field of Search ..................... 703/1, 7; 702/34; 73/7, 9, 10

(56) References Cited

U.S. PATENT DOCUMENTS 1,576,453 A   4/1926   Nordstrom .................. 33/533

(List continued on next page.)

FOREIGN PATENT DOCUMENTS

| SU | 161555 | 3/1964 |
| SU | 473079 | 6/1975 |
| SU | 479017 | 7/1975 |

OTHER PUBLICATIONS

Product Description: CD 102 High Speed Reciprocating Machine [online]. Plint & Partners, LTD [retrieved on Aug. 18, 2000]. Retrieved from the Internet: <URL: www.plint.co.uk/at2/leaflet/cd102.htm>.*

Product Description: TE 77 High Frequency Friction Machine [online]. Plint & Partners, LTD [retrieved on Aug. 18, 2000]. Retrieved from the Internet: <URL: www.plint.co.uk/at2/leaflet/te77.htm>.*

Tribology Update: Issue 6 [online]. Plint & Partners, LTD, Sep. 1996 [retrieved on Aug. 18, 2000]. Retrieved from the Internet: <URL: www.plint.co.uk/at2/update/issue6.htm>.*

Tribology Update: Issue 5 [online]. Plint & Partners, LTD, Mar. 1994 [retrieved on Aug. 18, 2000]. Retrieved from the Internet: <URL: www.plint.co.uk/at2/update/issue5.htm>.*

Hill, S. et al. "Bench Wear Testing of Common Gasoline Engine Cylinder Bore Surface/Piston Ring Combinations," STLE Tribology Transactions, vol. 39, No. 4, 1996. pp. 929–935.*

Malaczynski, G. et al. "Ion Implantation and Diamond–Like Coating of Aluminum Alloys," Journal of Materials Engineering and Performance, vol. 6, No. 2, Apr. 1997. pp. 223–239.*

*Primary Examiner*—Kyle J. Choi
(74) *Attorney, Agent, or Firm*—Rohm & Monsanto, P.L.C.

(57) ABSTRACT

A bench testing system creates a predetermined wear and friction environment wherein wear elements, illustratively a piston ring and a cylinder liner, can be tested, along with lubricant properties, under simulated conditions of an internal combustion engine. The effects of speed and normal load can be examined under multiple lubrication regimes, and variations in the coefficient of friction can be observed as a function of crank angle degree. Profilocorder techniques are used to examine photomicroscopic surface characteristics. The cylinder wall wear element is supported in a first support arrangement that is driven reciprocatingly along a substantially axial path. A dynamic counter-reciprocating arrangement is coupled thereto for controlling second harmonic inertial forces. A second support arrangement that supports the piston ring wear element is coupled to a linear drive that urges same in a direction transverse to the substantially axial path of reciprocation of the cylinder wall wear element. A force gauge coupled to the linear drive produces data corresponding to the force being applied thereby. A further force gauge measures the friction force. Rotational data is obtained from a rotational encoder, and a lubricant supply arrangement provides lubrication in accordance with a plurality of lubrication regimes.

61 Claims, 6 Drawing Sheets

U.S. PATENT DOCUMENTS

| | | | |
|---|---|---|---|
| 3,641,807 A | * 2/1972 | Brooks | 73/7 |
| 3,750,459 A | 8/1973 | Williams et al. | 73/49.4 |
| 3,783,681 A | 1/1974 | Hirt et al. | 73/119 |
| 3,861,223 A | * 1/1975 | Braun | 74/44 |
| 3,946,602 A | 3/1976 | Huntington et al. | 73/120 |
| 4,116,051 A | 9/1978 | Laib et al. | 73/116 |
| 4,174,627 A | 11/1979 | Swis et al. | 73/116 |
| 4,936,135 A | * 6/1990 | Annis et al. | 73/7 |
| 5,007,284 A | 4/1991 | Slone | 73/120 |
| 5,282,397 A | * 2/1994 | Harkness et al. | 74/603 |
| 5,557,039 A | * 9/1996 | Annis et al. | 73/7 |
| 6,094,967 A | * 8/2000 | Cavdar | 73/9 |

\* cited by examiner

RECIPROCATING SYSTEM FOR SIMULATING FRICTION AND WEAR

BACKGROUND OF THE INVENTION

1. Field of the Invention

This invention relates generally to systems for simulating wear conditions, and more particularly, to an arrangement and method of simulating friction environments, such as the friction conditions between components of an internal combustion engine.

2. Description of the Related Art

A significant portion of engine power within an internal combustion engine is lost as result of friction between the piston ring(s) and cylinder bore(s). There is need in the field of engine manufacture for a system that characterizes the frictional and wear characteristics of existing and new materials, so that their suitability for application within the various components of engines can be determined. Most commonly, gray iron is used as the cylinder bore material. This material is characterized as having good wear resistance due to hard carbide particles within it, but also a measure of lubricity is achieved by the graphite flakes contained therewithin which behave as a solid lubricant. Thus, the tribological properties of iron has resulted in cast iron liners being pressed or cast into aluminum engine blocks.

Aluminum alloys, thermal spray coated cylinder liners, and powder metal composites that contain solid lubricants have shown promising characteristics that may render these materials suitable as future cylinder bore material. However, extensive experimentation is required to understand the physical mechanisms of friction in cylinder liner-piston ring frictional contact.

Conventional friction and wear testing systems may include a pin on a disk, or block on a ring for testing. It is a problem with these known arrangements that they cannot simulate the operating conditions within an internal combustion engine. In fact, these known arrangements cannot produce reciprocating motion that would simulate the piston ring/cylinder wall interface in an internal combustion engine. The microstructure of a thermal spray coating that has been sprayed directly on to flat plates or rings is not representative of the microstructures obtained by spraying directly onto the cylinder gold liner surface. Thus, the use of actual engine components is highly desirable when simulating the friction environment in an engine, in order to maintain the actual geometry of the surface as well as its texture and microstructure.

It is a problem with known arrangements that test actual engines that they are expensive and their use is quite time consuming. Additionally, extensive modification of engine components is required. Gas and inertia forces are large compared to friction forces, and the temperature, load, and lubricant rate cannot be maintained constant during operation. It is additionally desired to distinguish the friction forces that result from the compression rings, from those that result from the oil ring, the piston skirt, and the bearings.

Current bench test systems have either very small stroke length and contact area, or low running speeds, which do not result in a close simulation of the actual engine conditions. There is, therefore, a need for an arrangement and a method of simulating frictional environments, that yield test results that are representative of the desired environment, such as the interior of an internal combustion engine, and which are repeatable to facilitate evaluation of advanced materials and lubricants.

The prior art has endeavored to produce wear testing systems that employ reciprocating motion. In one such system, an entire piston ring is positioned in a disk shaped holder, and the installed ring is reciprocated between static liner segments using a short stroke, on the order of one inch. This permits only small liner samples to be tested, two at a time. It is a problem with this known arrangement that its use limited to a short stroke at a relatively low running speed due to unbalanced inertia forces. It is a further problem that the disk-shaped holder that holds the complete piston ring is not representative of an actual piston. Still another problem with this known arrangement is that it is incapable of achieving simulation of various lubrication regimes.

It is, therefore, an object of this invention to provide a friction and wear simulation system that can be installed on a laboratory bench.

It is another object of this invention to provide a wear and friction simulation system that closely approximates a conditions encountered within an internal combustion engine.

It is also an object of the is invention to provide a friction and wear simulation system that can be operated at high speeds.

It is a further object of this invention to provide a wear and friction simulation system that allows a reciprocating stroke length corresponding to that of an actual internal combustion engine.

It is additionally an object of this invention to provide a wear and friction simulation system that enables testing at a plurality of lubricant delivery regimes.

SUMMARY OF THE INVENTION

The foregoing and other objects are achieved with this invention which provides, in a first apparatus aspect thereof, a system for simulating a friction environment between first and second wear elements in frictional communication with one another. In accordance with the invention, a first support arrangement supports the first wear element, and a reciprocating drive arrangement drives the first support arrangement reciprocatingly along the substantially axial path of reciprocation. A dynamic counterbalance arrangement is coupled to the reciprocating drive arrangement, and serves to nullify second order harmonic mechanical energy. A rotatory drive coupler is coupled to both, the reciprocating drive arrangement and the dynamic counterbalance arrangement. The rotatory drive coupler receives rotatory drive from a motor. A second support arrangement is provided for supporting the second wear element. A linear drive is coupled to the second support arrangement and urges same in the direction that is transverse to the substantially axial path of reciprocation. An electrical force signal responsive to a force applied by the linear drive to the second support arrangement is produced by a force gauge that is coupled to the linear drive.

In one embodiment of the invention, the second support arrangement is arranged to enable a transverse displacement of the second wear element with respect to the frictional communication with a first wear element. Thus, in embodiments of the invention where the second wear element is a portion of a piston ring, the ring portion is enabled to travel circumferentially for a limited distance within a groove that accommodates same within the second support arrangement. The second support arrangement may be, in certain embodiments, a portion of an actual piston of an internal combustion engine.

In another embodiment of the invention, the second support arrangement enables a transverse displacement of the second wear element with respect to the frictional communication with the first wear element. Again, in an embodiment of the invention where the second wear element is a portion of a piston ring on an internal combustion engine, the ring is permitted to tilt within the groove that accommodates same within the second support arrangement. Also, as stated, the second support arrangement in this embodiment of the invention may be a portion of a piston of an internal combustion engine.

In a further embodiment a rotational encoder produces and electrical signal that contains rotatory information relating to a rotational position of the rotatory drive coupling arrangement. In this manner, a signal is generated that permits instantaneous identification of the angular position of the rotatory drive coupler, and correspondingly, the first support arrangement. In an advantageous embodiment of the invention, the rotatory information contained within the electrical signal produced by the rotational encoder is correlated against the electrical force signal produced by the force gauge, whereby information in the form of a graphical representation can be provided corresponding to friction force as a function of angular displacement of the rotatory drive coupler. In a still further embodiment, a clock, which may be within a CPU, provides a time signal which, when correlated against, the rotatory information relating to the rotational position of the rotatory drive coupler produces instantaneous speed information.

In a practical embodiment of the invention, mechanical rotatory energy from the motor is delivered to the rotatory drive coupler by a power transfer belt. In a further embodiment, a rotatory inertial mass is coupled to the rotatory drive coupler to reduce angular speed variations. The rotatory inertial mass may be, in certain embodiments, a massive pulley that engages with the power transfer belt.

In a further embodiment, the first support arrangement includes a support bed for holding the first wear element, and a support guideway arrangement coupled to the support bed for constraining the support bed to travel along a substantially axial path of reciprocation. The support guideway includes, an elongated rail arranged parallel to the substantially axial path of reciprocation. Additionally, a linear bearing coupled to the support bed is slidingly movable along the elongated rail. Preferably, two such rails and correspondingly associated linear bearings insure that the support bed is urged reciprocatingly along a straight or axial pathway. In an embodiment of the invention where the frictional environment to be simulated constitutes the interior of an internal combustion engine, the first wear element is a portion of a cylinder wall, and a second wear element, as previously stated is a portion of a piston ring of an internal combustion engine.

The rotatory coupler, in a practical embodiment of the invention, constitutes a crank arrangement that has first and second crank portions radially displaced from one another. The reciprocating drive arrangement is coupled to the first crank portion, and the dynamic counterbalance arrangement is coupled to the second crank portion. As will be described herein, this crank arrangement permits the dynamic counterbalance arrangement to travel counter-reciprocatingly to achieve the desired balancing out of the second harmonic mechanical energy. Residual unbalance of the crank arrangement is corrected by the use of one or more balancing weights coupled thereto.

The dynamic counterbalance arrangement constitutes, in a highly advantageous embodiment of the invention, a counterweight that is urged in response to the reciprocating drive arrangement to travel reciprocatingly along a further substantially axial path of reciprocation. Preferably, this path is parallel to the substantially axial path of reciprocation of the support bed. In a preferred embodiment, two such counterweights are used in parallel. Each counterweight is provided with a guideway that constrains same to travel along respective substantially axial paths of reciprocation. The reciprocating travel by the reciprocating drive arrangement along the substantially axial path of reciprocation, and the reciprocating travel of the counterweight along the further substantially axial path of reciprocation, are out of phase with one another, and preferably 180° out of phase. Thus, the relative motion is counter-reciprocatory. With respect to the linear drive that urges the second wear element toward the first wear element, there is provided a linear actuator that produces a linear force in a predetermined direction. Additionally, a cantilever arrangement delivers the linear force to the second support arrangement. In a preferred embodiment, the linear actuator is a pneumatic cylinder/piston assembly. An air regulator, which in some embodiments may be responsive to a CPU, controls the magnitude of the linear force applied by the pneumatic cylinder/piston assembly. A pivot coupling is provided for the cantilever member whereby the linear force is delivered to the second support arrangement in the direction that is opposite to the predetermined direction of linear force provided by the cylinder/piston assembly. A compression element couples the lever member to the second support arrangement. The force gauge, which may be a piezoelectric strain gauge is coupled to the compression member.

There is additionally provided a lubrication arrangement for delivering a lubricant to the first and second wear elements. The lubrication arrangement includes a pump for pumping the lubricant, and a nozzle for delivering the pumped lubricant to a predetermined location in relation to the first and second wear elements. A lubricant metering arrangement controls the rate of delivery of the lubricant to a predetermined flow rate. Illustratively, the flow rate is approximately between 0.2 $\mu$l per h and 500 ml/h.

Temperatures controlled by a temperature control arrangement that may include a heater for delivering heat to the frictional wear interface, and a temperature monitoring arrangement, such as a thermal couple. In an embodiment of the invention that endeavors to simulate the internal characteristics of an internal combustion engine, the temperature is controlled to a range of approximately between 400° C. and 600° C.

In accordance with a further apparatus aspect of the invention, there is provided a system for collecting correlatable data responsive to a simulated friction environment between a cylinder wall wear element and a piston ring wear element, that are in frictional communication with one another. In accordance with the invention, there is provided a first support arrangement for supporting the cylinder wall wear element, and a reciprocating drive arrangement that drives the first support arrangement reciprocatingly along a substantially axial path of reciprocation. As previously indicated, a dynamic counter-reciprocating arrangement is coupled to the reciprocating drive arrangement for controlling the second harmonic inertial forces. A crank is coupled to the reciprocating drive arrangement and to the dynamic counter-reciprocating arrangement. A rotatory drive is coupled to the crank for supplying a rotatory mechanical energy thereto. A second support arrangement supports the piston ring wear element, and a linear drive is coupled to a second support arrangement for urging same in a direction that is transverse to the substantially axial path of reciprocation. The force is measured by a force gauge that is coupled to the linear drive for producing an electrical force signal that is responsive to the force applied by the linear drive to the second support arrangement. Lubrication is provided by a lubricant supply arrangement that delivers a lubricant to a predetermined side of the piston ring wear element. A rotational encoder produces an electrical rotatory data signal that contains rotatory information relating to a rotational position of the crank coupling arrangement.

In one embodiment of this further apparatus aspect of the invention, there is provided a data correlation arrangement for correlating the electrical force signal against the rotatory information in the electrical rotatory data signal. The rate of delivery of the lubricant is controlled by a lubricant supply flow rate controller which controls the flow rate to a predetermined flow rate within a range of approximately between 0.2 $\mu$l/h and 500 ml/h. A controllable lubricant drain controls accumulation of the lubricant.

As previously noted, temperature is controlled by a temperature control arrangement that includes a thermocouple that is thermally in communication with the piston ring wear element. The linear actuator includes a pneumatic cylinder/piston assembly that receives regulated air for controlling the linear force applied by the pneumatic cylinder/piston assembly.

Variations in system speed are reduced by the use of a rotatory inertial mass coupled to the crank. As previously indicated, the rotatory inertial mass may be a pulley.

In an advantageous embodiment of the invention, the second support arrangement includes a two-point load transfer arrangement coupled to the piston ring wear element for enabling a frictional communication between the piston ring wear element and the cylinder wall wear element to be responsive to a resilience characteristic of the piston ring wear element. Circumferential and tilt displacements of the piston ring wear element with respect to the cylinder wall wear element are enabled in certain embodiments of the invention.

In accordance with a first method aspect of the invention, there is provided a method of collecting correlatable data responsive to a simulated friction environment between first and second wear elements in frictional communication with one another. The method includes the steps of:
first driving the first wear element along a predetermined path of reciprocation;
second driving a dynamic counter-reciprocating arrangement;
supporting the second wear element;
third driving the second support arrangement in a direction transverse to the predetermined path of reciprocation;
first producing an electrical force data signal responsive to a force applied the second wear element to the first wear element in response to the step of third driving; and
second producing an electrical rotatory data signal containing position information in response to the step of first driving.

In one embodiment of this method aspect of the invention, there are provided the further steps of:
calculating an instantaneous coefficient of friction for the frictional communication between first and second wear elements; and
correlating the instantaneous coefficient of friction to the electrical rotatory data signal.

In a further embodiment, the step of calculating an instantaneous coefficient of friction includes the further steps of:
first determining a friction force of the simulated friction environment between the first and second wear elements; and
calculating a ratio of the friction force of the simulated friction environment and the data in the electrical force data signal.

In a further embodiment, there is provided the further step of repeating the steps of calculating and correlating at each of a plurality of respective rates at which the step of first driving is performed.

In a further embodiment, there is provided the step delivering a predetermined quantity of lubricant to the region of frictional communication between the first and second wear elements. There is additionally provided the step of repeating the steps of calculating an correlating at each of the plurality of respective predetermined quantities of lubricants during the step of first driving. Thus, a friction environment can be created for various lubrication regimes.

In a further embodiment, there is provided the step of timing the electrical rotatory data signal for producing a speed signal.

In accordance with a further method aspect of the invention, there is provided a method of collecting correlatable data responsive to a simulated friction environment between first second and second wear elements in frictional communication with one another in accordance with the invention, the method includes the steps of:
first driving the first wear element along a predetermined path of reciprocation;
second driving a dynamic counter-reciprocating arrangement;
supporting the second wear element in a predetermined spatial relation to the first wear element;
third driving the second support arrangement in a direction transverse to the predetermined path of reciprocation; and
measuring a roughness characteristic of at least a selected one of the first and second wear elements.

In one embodiment of this further method aspect of the invention, the step of measuring includes the step of forming an optical photo-microscopic evaluation of the selected one of the first and second wear elements. The optical photo-microscopic evaluation contains information relating to distribution of the roughness characteristic over a predetermined surface area of the selected one of the first and second wear elements. In a further embodiment, the step of measuring includes the step of correlating a roughness characteristic of the selected one of first and second wear elements to a distance there along.

BRIEF DESCRIPTION OF THE DRAWING

Comprehension of the invention is facilitated by reading the following detailed description, in conjunction with the annexed drawing, in which.

DETAILED DESCRIPTION

Figure 1:
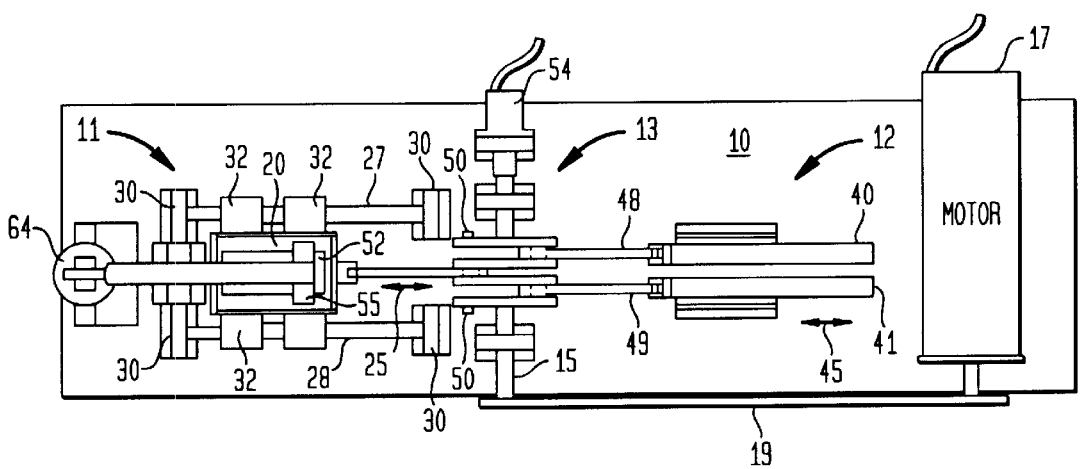
FIG. 1 is a simplified schematic top plan view of a specific illustrative embodiment of the invention.

FIG. 1 is a simplified schematic top plan view of a friction environment system 10 having a wear testing portion 11, a counter-balance portion 12, and a crank drive portion 13. The crank drive portion is coupled via a shaft 15 and a pulley (not shown) to a motor 17 via a drive belt 19.

Wear testing portion 11 has a first support element 20 that is connected by a connecting rod 22 to crank drive portion 13. As crank drive portion 13 is rotated by operation of motor 17, first support element 20 is driven by connecting rod 22 reciprocatingly in the direction of two-headed arrow 25. The first support element is constrained to axial reciprocating motion by virtue of its coupling tool linear rails 27 and 28, which are maintained in fixed parallel relation to one another by rail supports 30. A plurality of linear bearings 32 are coupled to first support element 20 and to respective ones of linear rails 27 and 28. Thus, the first support element is constrained to linear motion, as noted hereinabove.

In this specific illustrative embodiment of the invention, counter-balance portion 12 is provided with a pair of counter-balance pistons 40 and 41 that are constrained by piston guideways 42 and 43 to travel in linear parallel paths of reciprocation in the direction of two-headed arrow 45. Counter balance pistons 40 and 41 are coupled to crank drive portion 13 by respectively associated connecting rods 48 and 49. As shown, the counter-balance pistons are arranged 180° out of phase with the coupling of first support element 20 to the crank drive portion via connecting rod 22, and therefore the counter balance pistons travel in opposite directions of reciprocation with respect to the first support element. This counter balancing action eliminates second harmonic inertial forces. Crank drive portion 13 is itself balanced by balance weights 50 which serve to correct any residual unbalance therein. In addition, crank drive portion 13 is shown to be coupled to a rotatory encoder 54 that produces an electrical signal responsive to the angular position of the crank drive portion. The operation of the rotatory encoder will be described below in connection with FIG. 2.

FIG. 1 further shows a first wear element, which in this embodiment of the invention is a cylinder portion 52, disposed on first support element 20. Thus, cylinder portion 52 is moved reciprocatingly with the first support element. A second support element which in this embodiment is a portion of a piston ring (not shown) is installed on a second support element 55 and as will be described herein below with respect to FIG. 2, is urged into frictional communication with cylinder portion 52.

Figure 2:
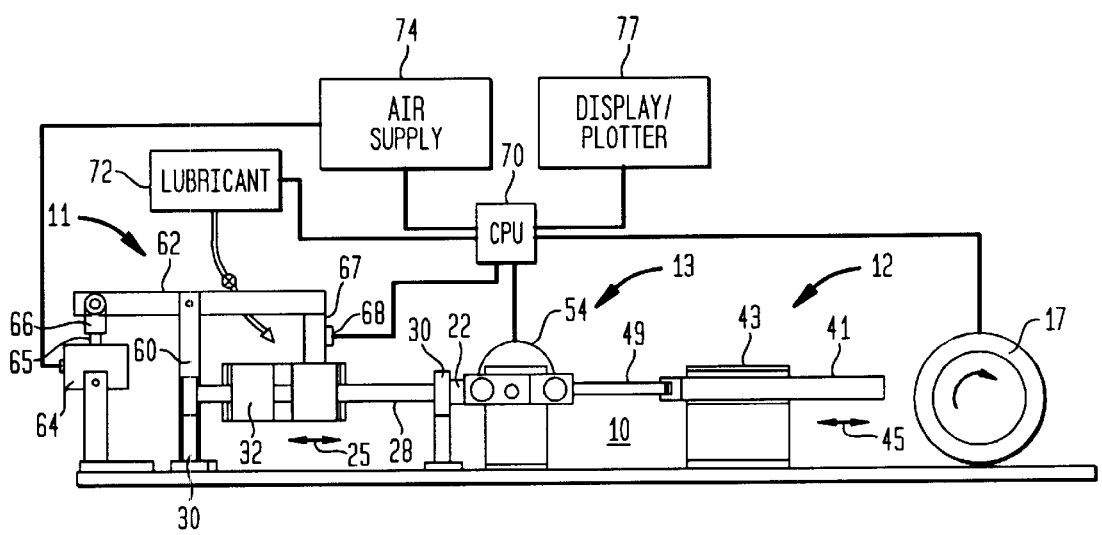
FIG. 2 is a simplified schematic side view of the embodiment of FIG. 1 further showing related systems in schematic function block form.

FIG. 2 is a simplified schematic side view of the embodiment of FIG. 1. Elements of structure that have previously been discussed are similarly designated. Wear testing portion 11 is shown to have a stanchion 60 on which is pivotally supported a cantilever 62. Cantilever 62 is coupled at its left-hand side to a linear actuator, which in this embodiment of the invention is a pneumatic cylinder 64 with a piston 65 extending upwardly therefrom. A force gauge 66, which may be a piezoelectric strain gauge, is installed in piston 65 to provide a signal responsive to the force exerted by the piston. Second support element 55 (not shown in this figure) is connected at the lower most end of a compression member, in the form of coupler element 67. Thus, as pneumatic cylinder 64 is energized with compressed air (not shown), piston 65 is urged upwardly against cantilever 62 which then applies a downward force on coupler element 67. In addition, however, coupler element 67 is subject to lateral forces that correspond to the friction force resulting from friction between cylinder portion 52 and the piston ring (not shown) installed on a second support element 55. The normal force applied to coupler element 67 corresponds to the force applied by pneumatic cylinder 64. However, the lateral force corresponds to the friction force between the wear elements. In embodiments where the normal force is monitored by force gauge 66, the friction force is monitored by a strain gauge 68, which may be a piezoelectric device.

It can be seen that although second support element 55 is urged downward by operation of the linear drive effected by pneumatic cylinder 64 and its associated piston 65, the second support element is maintained substantially immobile in the direction of travel of first support element 20 and cylinder portion 52.

FIG. 2 further shows a schematic representation of a CPU 70 of the type that contains logic and timing circuitry (not specifically designated). CPU 70 receives data from rotary encoder 54 and strain gauge 68. It is to be understood that strain gauge 68 is but a schematic representation of a full bridge circuit that provides data corresponding to the compression force being applied via coupler element 67 and a lateral drag force (not specifically designated) that corresponds to a friction force between cylinder portion 52 and the ring portion installed on second support element 55 (not shown in this figure).

In this specific illustrative embodiment of the invention, CPU 70 controls a lubricant supply 72 which is shown to direct a lubricant to the region where the cylinder portion and the piston ring portion communicate frictionally. In addition, CPU 70 controls the delivery of air from an air supply 74 to a pneumatic cylinder 64. In this manner CPU 70 can control the linear force being applied via piston 65.

Further in this specific embodiment, in addition to timing the encoder data received from rotatory encoder 54, CPU 70 can provide control signals to motor 17. The results of the computation and correlations performed by CPU 70, as will be discussed herein below, are displayed on a display or plotter 77.

Figure 3:
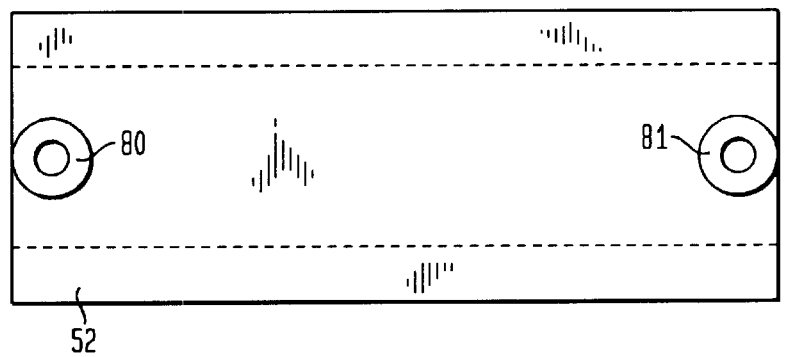
FIG. 3 is a plan representation of a cylinder bore segment employed in the practice of the invention.

FIG. 3 is a schematic plan view of cylinder portion 52. As shown, cylinder portion 52 is cut into a rectangular plan configuration, illustratively 50.8 millimeters wide and 127 millimeters long. The cylinder portion is provided with apertures 80 and 81 therethrough for accommodating respective fasteners (not shown) therethrough whereby the cylinder portion is fixed onto first support element 20 (not shown in this figure).

Figure 4:
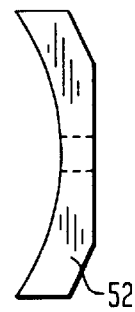
FIG. 4 is a side representation of the cylinder bore segment of FIG. 3.

FIG. 4 is a side representation of cylinder portion 52 of FIG. 3. In this embodiment of the invention, an expanding type mandrel (not shown) is used to cut the cylinder portion samples in order to preserve cylinder access and uniform sample thickness. Apertures 80 and 81 are countersunk to permit the use of flat head screws as the fasteners. Alignment is achieved by means of adjusting screws (not shown) associated with linear bearings 30 (not shown in this figure). In the practice of the invention, the cylinder portion samples are aligned using an analog dial indicator (not shown) having an accuracy of ±0.001 inch. In this specific application of the invention cylinder portion 52 has an internal curvature corresponding to a diameter of 89 millimeters.

In this application of the invention, the following testing conditions were observed:

TABLE 1

STANDARD TESTING CONDITIONS

| | |
|---|---|
| Speed | : 500 rpm |
| Ring Normal Load | : 80N |
| Temperature | : 26° C. |
| Lubricant | : Mobile 5W30 motor oil |
| Lubricant rate | : 10 ml/h |
| Material | : Cast iron cylinder liner vs. chromium plated ring |

The bench testing system of the present invention has been used, as described here in above, to measure piston ring and cylinder liner friction for realistic stroke and speeds. The present invention permits simulated conditions such as speed and ring load to be investigated when other test conditions are held constant.

In the specific illustrative embodiment of the invention described herein above, the reciprocation movement of cylinder portion 52 is responsive to the rotary energy supplied by motor 17, which may be a one horsepower Dayton DC motor. As previously mentioned, strain gauge 68 is a two-axis force sensor designed to measure normal force and friction force. Inertial forces along the horizontal access are balanced by counter balance pistons 40 and 41 in counter-balance portion 12 of friction environment system 10 which run in a reciprocating motion that is counter to that of cylinder portion 52. Rotational inertia forces are balanced using counterweights, in the form of balance weights 50 installed on the crank shaft arms (not specifically designated). Moreover, a large crank shaft pulley (not shown), which is coupled to shaft 15 and drive belt 19 functions additionally as an inertia disk that minimizes variations in angular speed.

In a further embodiment of the invention, frictional environment system 10 is monitored on a Newport air table in order to isolate same from the laboratory floor (not shown). Needle type roller bearings (not shown) and oil filled bronze bearings (not shown) are used in the connecting rods, whereby periodic maintenance lubrication of the crank shaft is obviated.

The system of the present invention controls the speed, temperature, lubricant amount, lubricant process, friction force, loading force, crank angle signal, and contact temperature data, simultaneously. In some embodiments where the speed of motor 17 is not controlled by CPU 70 a Dayton DC speed controller may be used. Rotatory encoder 54 may be a BEI motion model H25 encoder. In a practical embodiment, rotatory encoder 54 is connected such that 360 increments per revolution and a single signal per revolution, can be read separately. In embodiments where CPU 70 is not coupled to rotatory encoder 54, running speed can be monitored using a Hewlett-Packard 5314A type-MHZ universal counter. Since the running speed, crank radius, and connecting rod length are known, sliding velocity of the ring can be calculated. In a further embodiment, surface temperature is measured by a Type Copper-Constantan thermal couple (not shown) attached to the piston ring holder. An Omega CN 76020 type temperature controller and an Omega strip heater system (not shown) are used to simulate actual engine cylinder liner temperature. Surface temperature can be increased up to 100° C. using the heater system.

In embodiments of the invention where the lubricant supply is not connected to CPU 70, lubricant rate can be controlled by a Cole Palmer 749000 syringe pump. Flow rate can be adjusted from 0.2 μl/h to 500 ml/h range with an accuracy of ±0.2%. In this embodiment, a 60 ml syringe is filled with lubricant and dripped behind the ring holder. Excess lubricant is drained through a hole (not shown) that is drilled through the liner holder. The drain hole is controllable in that it can be closed with a screw (not shown) so that wear samples can be tested under fully flooded lubrication conditions.

In a practical embodiment of the invention, the following specifications are used for friction environment simulator system 10:

| | | | |
|---|---|---|---|
| Stroke (2x crank radius) | : | 84 | millimeters |
| Connecting Rod Length | : | 142 | millimeters |
| Maximum DC motor speed | : | 1750 | rpm |
| Maximum running speed | : | 750 | rpm |
| Maximum ring normal load | : | 360 | N |

Second support element 55, which supports the piston ring (not shown), is configured to create a predetermined contact area between the piston ring portion and the cylinder portion. As previously indicated, actual piston and ring segments have been used as the ring holder. The ring is free to rotate in the piston groove and is constrained from each side of the piston by set screws (not shown). A normal load is applied to the rings segments using two doll pins (not shown) so that the elasticity of the ring can be utilized to create the predetermined area contact between the piston ring and cylinder liner segments. In addition, the piston ring is permitted to tilt within the groove, to simulate with further accuracy the actual conditions within an internal combustion engine (not shown).

As indicated hereinabove with respect to FIGS. 1 and 2, second support element 55 is connected to coupler element 67, which operates as a loading arm, the normal force applied thereto being supplied by cantilever 62, and the lateral force being responsive to the friction force. In this specific illustrative embodiment of the invention, strain gauge circuit 68 measures instantaneous friction force between the piston ring and cylinder liner. For this purpose, MM WK-06-062AP-350 strain gauges are placed on the cantilever force sensor in a full bridge configuration. Applied dynamic normal load is measured by an Omega load sensor connected between the air cylinder and the loading arm, in this embodiment.

The strain gauges are compensated for variations in temperature. Since the stresses in the cantilever are held within the elastic region, the strain gauge circuits produce a voltage that is proportional to friction force and normal load. In some embodiments, the strain gauge signals are amplified using Measurements Group 2311 signal conditioning amplifiers. The force gauge is calibrated for normal load and friction force using known weights (not shown).

In some embodiments, a Data 61000 data acquisition system is used to collect data. Collected data is processed by a CPU. A top-dead center signal that is issued by the rotary encoder can be used to trigger an oscilloscope (not shown).

In this embodiment, the crank angle signal derived from the rotary encoder is used as an external clock, and voltages produced by the strain gauges, which are proportional to friction force load and dynamic normal load, are recorded for every crank angle degree.

As will be described hereinbelow, the effects of simulated conditions such as speed and ring load have been investigated while other test conditions are held constant. The friction behavior is consistent with a mixed lubrication regime. The existence of high friction force values near dead centers indicate metal to metal contact. As the ring speed increase friction force decrease significantly. This shows the transition between boundary to hydrodynamic lubrication. The following tests are described below:

TABLE 2

TEST MATRIX

| TEST # | SPEED | NORMAL RING LOAD |
|---|---|---|
| 1 | 500 rpm | 80N |
| 2 | 500 rpm | 160N |
| 3 | 700 rpm | 80N |
| 4 | 700 rpm | 160N |

Figure 5:
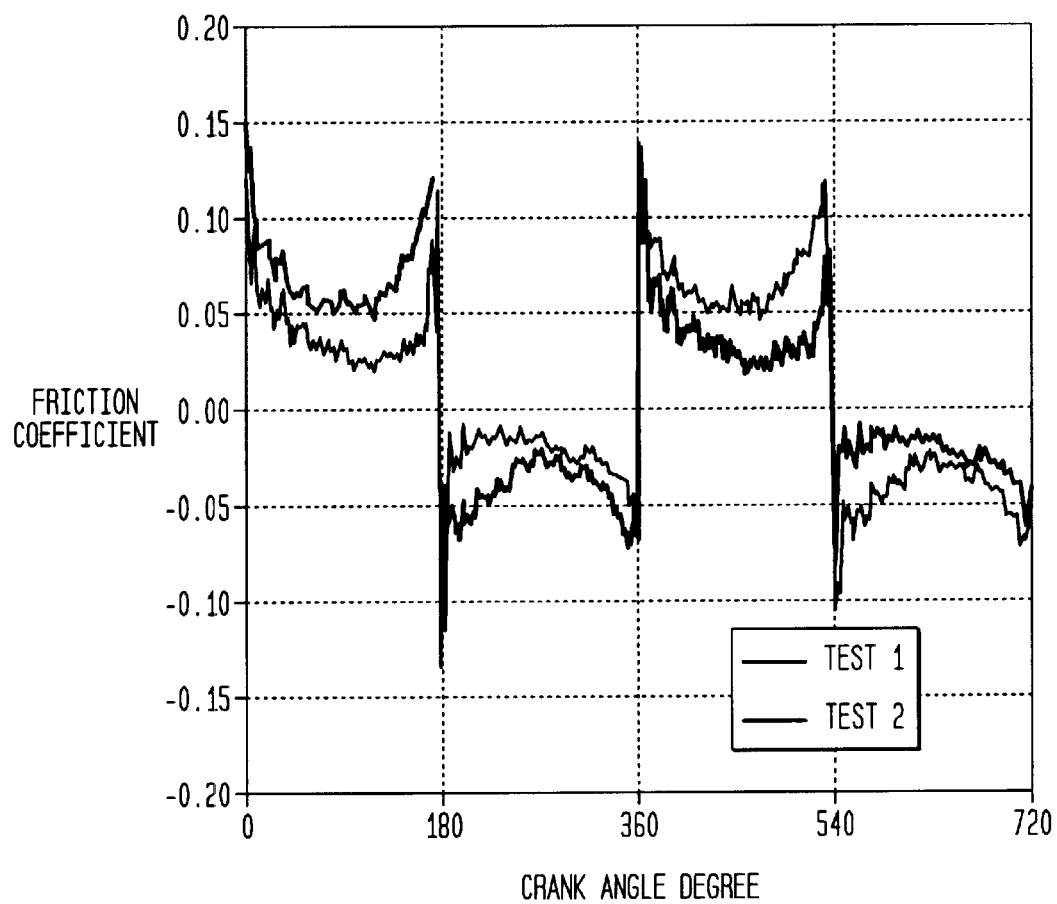
FIG. 5 is a graphical representation of the coefficient of friction plotted against crank angle for various loads.

FIG. 5 is a graphical representation of a plot of the coefficient of friction versus crank angle degree. Test 1 was conducted with a ring normal load of 80 N. In Test 2, the ring normal load was 160 N. The figure shows the change in friction coefficient for 80 N and 160 N ring normal loads, and that for higher ring normal loads, boundary lubrication dominates where a higher friction coefficient is found. However, near bottom dead center (180° crank angle degree) metal-to-metal friction is more significant for 160 N applied ring load. This, it is believed, may be explained as higher squeeze film effect occurring under light loads.

Figure 6:
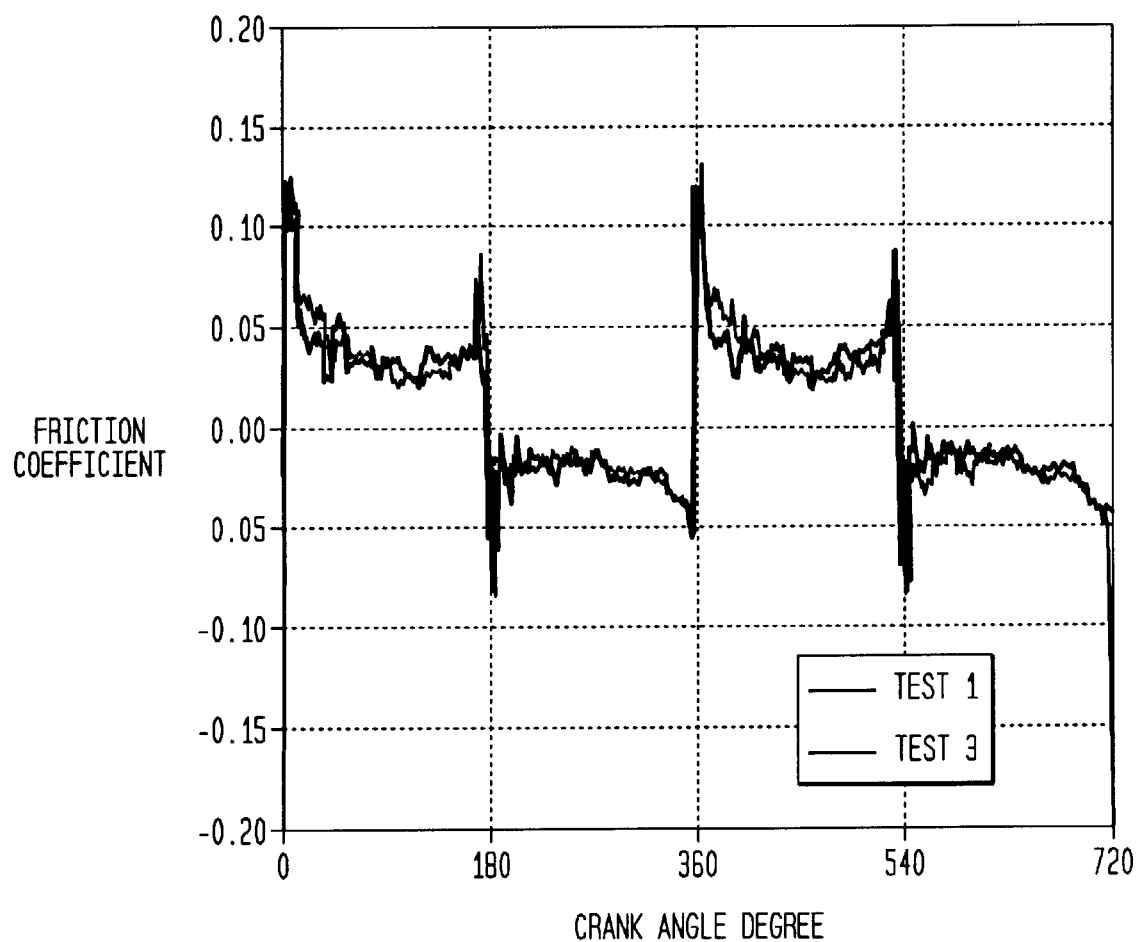
FIG. 6 is a graphical representation showing the coefficient of friction plotted against crank angle for various running speeds.

FIG. 6 is a further graphical representation of the coefficient of friction plotted against crank angle. In this set of tests, the running speed of Test 1 was 500 rpm. The running speed of Test 3 was 700 rpm. The friction coefficient is plotted over crank angle degree for 500 and 700 rpm running speeds under standard testing conditions (see, Table 1) for the remaining parameters. The results for the two different speeds are similar for light loads. Higher friction coefficients can be observed near center stroke where ring speed is high so that hydrodynamic lubricant effects are dominant.

Figure 7:
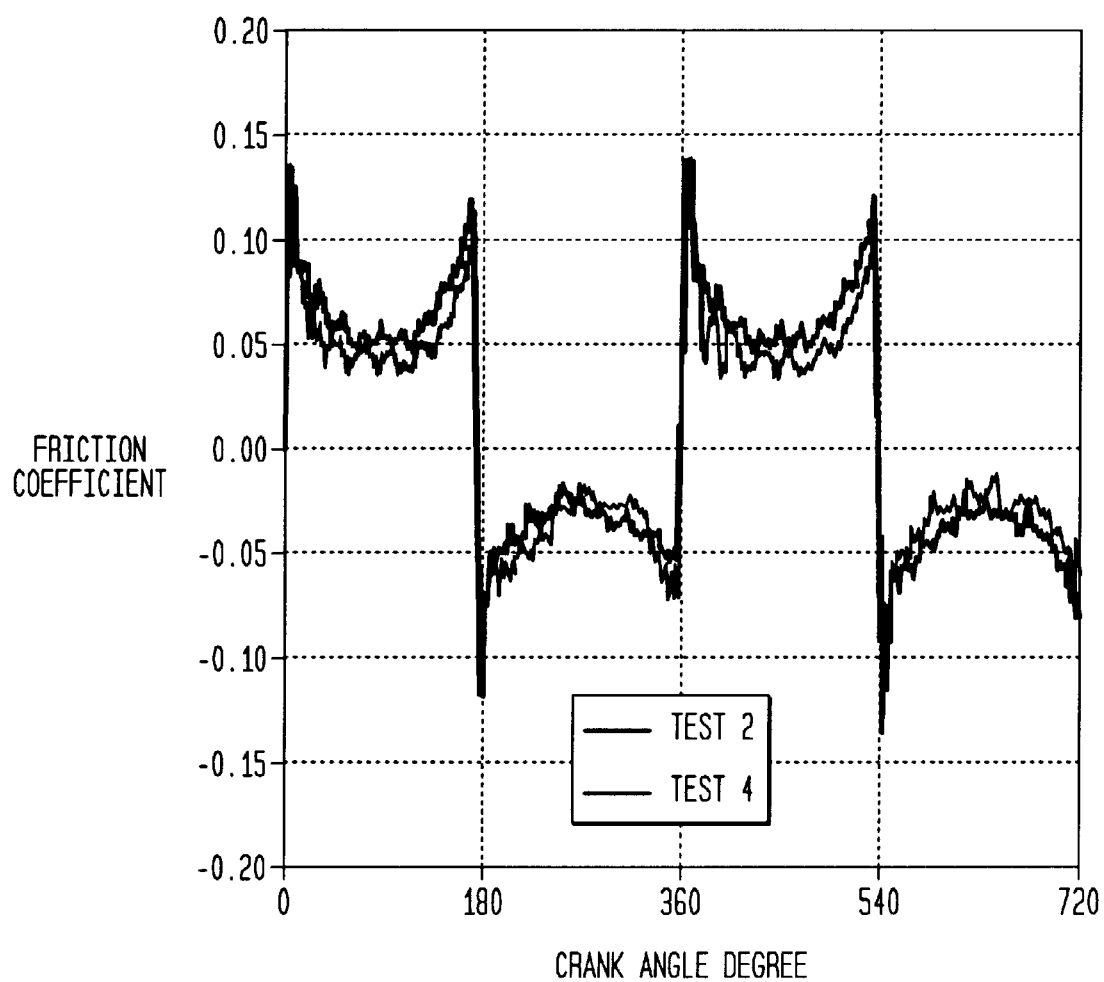
FIG. 7 is a graphical representation showing the coefficient of friction plotted against crank angle for a specific load at various operating speeds.

FIG. 7 is a graphical representation of friction coefficient plotted against crank angle degree. In this figure, ring normal load of 160 N was plotted in Test 2 at 500 rpm and in Test 4 at 700 rpm. Thus, in FIG. 7, the same speeds are compared for higher ring normal loads. The effect of speed can be observed more easily under higher ring loads where boundary lubrication dominates. Friction coefficient is shown to increase with increasing ring speed under mixed lubrication regime.

Figure 8:
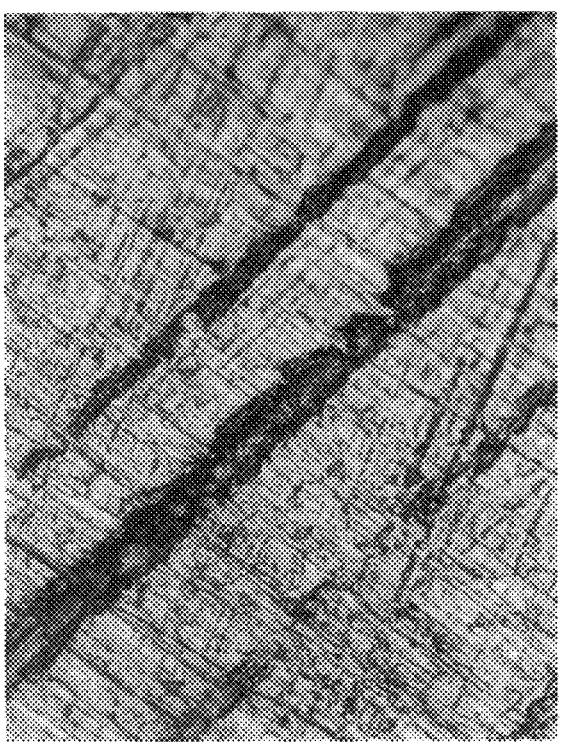
FIG. 8 is an optical photo-microscopic evaluation of a cast iron cylinder liner sample.
Figure 9:
FIG. 9 is an optical photo-microscopic evaluation of a powder metal cylinder liner sample.

FIGS. 8 and 9 are optical photomicroscopic evaluations of cylinder portion liner samples. FIG. 8 shows the photomicroscopic evaluation of cast iron while FIG. 9 shows a powder metal. The figure shows a honed surface finish pattern for the cast iron sample.

Figure 10:
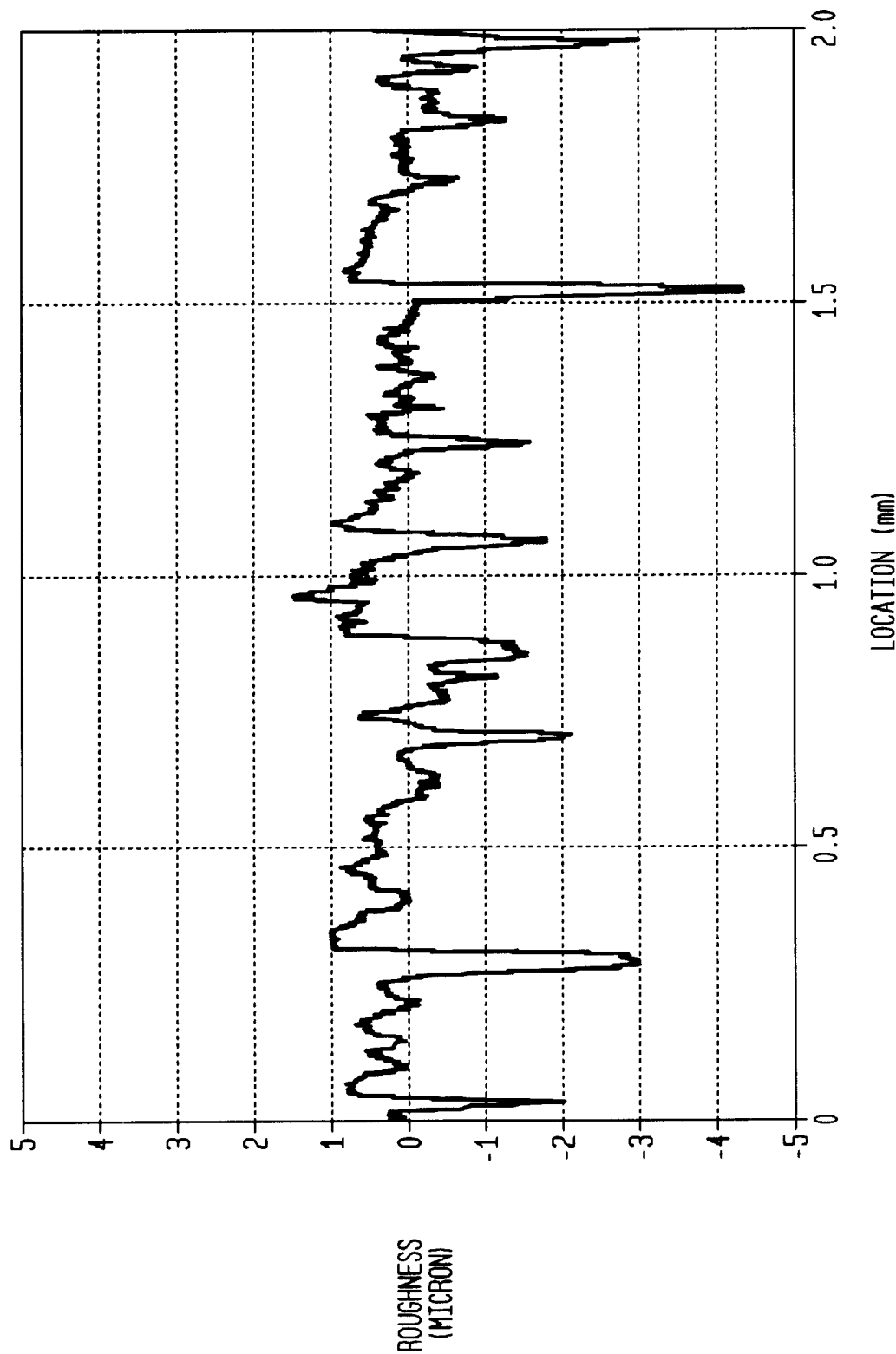
FIG. 10 is graphical representation of surface roughness plotted against location for a cast iron cylinder liner sample.

FIG. 10 is a graphical representation of roughness plotted against location for an unworn cast iron cylinder portion sample. Here, cut-off equals 0.8, Ra equals 0.47 μm, Rq equals 0.71 μm, and skew equals −2.2. The surface roughness of the liner samples was examined using a Suretronic Tallysurf surface analyzer. In order to minimize measurement errors, and non-uniform surface roughness effects, surface roughness of the samples was measured three times and traces with the highest and lowest Ra values were discarded.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A system for simulating a friction environment between first and second wear elements in frictional communication with one another, the system comprising:

a first support arrangement for supporting the first wear element;

a reciprocating drive arrangement for driving said first support arrangement reciprocatingly along a substantially axial path of reciprocation;

a dynamic counterbalance arrangement coupled to said reciprocating drive arrangement;

a rotatory drive coupling arrangement coupled to said reciprocating drive arrangement and to said dynamic couterbalance arrangement;

a motor coupled to said rotatory drive coupling arrangement for supplying a rotatory mechanical energy thereto;

a second support arrangement for supporting the second wear element, said second support arrangement being arranged to enable a tilt displacement of the second wear element with respect to the frictional communication with the first wear element, the tilt displacement of the second wear element being responsive to said reciprocating drive arrangement for simulating the frictional environment;

a linear drive coupled to said second support arrangement for urging same in a direction transverse to said substantially axial path of reciprocation; and a force gauge coupled to said linear drive for producing an electrical force signal responsive to a force applied to said second support arrangement.

2. The system of claim 1, wherein said second support arrangement is arranged to enable a transverse displacement of the second wear element with respect to the frictional communication with the first wear element.

3. The system of claim 1, wherein there is further provided a rotational encoder for producing an electrical signal containing rotatory information relating to a rotational position of said rotatory drive coupling arrangement.

4. The system of claim 3, wherein there is further provided a data correlation arrangement for correlating the electrical force signal to the rotatory information relating to a rotational position of said rotatory drive coupling arrangement.

5. The system of claim 3, wherein there is further provided a clock for providing a time signal containing temporal information for combining with said rotatory information for producing a speed signal responsive to an operating speed of the system for simulating the friction environment.

6. The system of claim 1, wherein there is further provided a belt-type power transfer arrangement for coupling said motor to said rotatory drive coupling arrangement.

7. The system of claim 1, wherein there is further provided a rotatory inertial mass coupled to said rotatory drive coupling arrangement for reducing angular speed variations of said rotatory drive coupling arrangement.

8. The system of claim 1, wherein said first support arrangement comprises:
   a support bed for holding the first wear element; and
   a support guideway arrangement coupled to said support bed for constraining said support bed to travel along the substantially axial path of reciprocation.

9. The system of claim 8, wherein said support guideway comprises:
   an elongated rail arranged parallel to the substantially axial path of reciprocation; and
   a linear bearing for coupling said support bed to said elongated rail.

10. The system of claim 9, wherein the first wear element is a portion of a cylinder wall of an internal combustion engine, and the second wear element is a portion of a piston ring of an internal combustion engine.

11. The system of claim 1, wherein said rotatory drive coupling arrangement comprises a crank arrangement having first and second crank portions displaced axially from one another, said reciprocating drive arrangement being coupled to said first crank portion and said dynamic counterbalance arrangement being coupled to said second crank portion.

12. The system of claim 11, wherein there is further provided a balancing weight coupled to said crank arrangement for correcting a residual unbalance thereof.

13. The system of claim 1, wherein said dynamic counterbalance arrangement comprises a counterweight that is urged in response to said reciprocating drive arrangement to travel reciprocatingly along a further substantially axial path of reciprocation.

14. The system of claim 13, wherein said dynamic counterbalance arrangement comprises a further counterweight that is urged in response to said reciprocating drive arrangement to travel reciprocatingly along a substantially axial path of reciprocation that is parallel to the further substantially axial path of reciprocation.

15. The system of claim 13, wherein there is further provided a counterweight guideway that constrains said counterweight to travel along said further substantially axial path of reciprocation.

16. The system of claim 13, wherein the reciprocating travel by said reciprocating drive arrangement along the substantially axial path of reciprocation and the reciprocating travel by said counterweight along the further substantially axial path of reciprocation are out of phase with each other.

17. The system of claim 16, wherein the reciprocating travel by said reciprocating drive arrangement along the substantially axial path of reciprocation and the reciprocating travel by said counterweight along the further substantially axial path of reciprocation are 180° out of phase with respect to each other, whereby their relative motion is counter-reciprocatory.

18. The system of claim 1, wherein said linear drive comprises:
   a linear actuator for producing a linear force in a predetermined direction; and
   a lever member for delivering the linear force to said second support arrangement.

19. The system of claim 18, wherein said linear actuator comprises a pneumatic cylinder/piston assembly.

20. The system of claim 19, wherein there is provided a further force gauge coupled to said pneumatic cylinder/piston assembly.

21. The system of claim 19, wherein there is further provided an air regulator for controlling the linear force applied by said pneumatic cylinder/piston assembly.

22. The system of claim 18, wherein there is further provided a pivot coupling for said lever member whereby the linear force is delivered to said second support arrangement in a direction opposite to the predetermined direction of the linear force.

23. The system of claim 22, wherein there is provided a coupling member for coupling said lever member to said second support arrangement, said force gauge being coupled to said coupling member for monitoring a friction force.

24. The system of claim 23, wherein said force gauge comprises a piezoelectric strain gauge.

25. The system of claim 1, wherein there is further provided a lubrication arrangement for delivering a lubricant to the first and second wear elements.

26. The system of claim 25, wherein said lubrication arrangement comprises:
   a pump for pumping the lubricant; and
   a nozzle for delivering the pumped lubricant to a predetermined location in relation to the first and second wear elements.

27. The system of claim 26, wherein there is further provided a lubricant metering arrangement for controlling the rate of delivery of the lubricant to a predetermined flow rate.

28. The system of claim 27, wherein said lubricant metering arrangement controls a rate of delivery of the lubricant to a predetermined flow rate within a range of approximately between 0.2 l/h and 500 ml/h.

29. The system of claim 26, wherein there is further provided a temperature control arrangement for controlling the temperature of the first and second wear elements.

30. A system for collecting correlatable data responsive to a simulated fiction environment between a cylinder wall wear element and a piston ring wear element in frictional communication with one another, the system comprising:
   a first support arrangement for supporting the cylinder wall wear element;
   a reciprocating drive arrangement for diving said fist support arrangement reciprocatingly along a substantially axial path of reciprocation;
   a dynamic counter-reciprocating arrangement coupled to said reciprocating drive arrangement for controlling second harmonic inertial forces;
   a crank coupling arrangement coupled to said reciprocating drive arrangement and to said dynamic counter-reciprocating arrangement;
   a rotatory drive coupled to said crank coupling arrangement for supplying a rotatory mechanical energy thereto;
   a second support arrangement for supporting the piston ring wear element, said second support arrangement being arranged to enable a tilt displacement of the piston ring wear element with respect to the frictional communication with the cylinder wall wear element, the tilt displacement of the second wear element being responsive to said reciprocating drive arrangement for simulating the frictional environment;
   a linear drive coupled to said second support arrangement for urging same in a direction transverse to said substantially axial path of reciprocation;
   a force gauge coupled to said linear drive for producing an electrical force signal responsive to a force applied by said linear drive to said second support arrangement;

a lubricant supply arrangement for delivering a lubricant to a predetermined side of the piston ring wear element; and a rotational encoder for producing an electrical rotatory data signal containing rotatory information relating to a rotational position of said crank coupling arrangement.

31. The system of claim 30, wherein there is further provided a force gauge coupled to said second support arrangement for monitoring a friction force between the cylinder wall wear element and the piston ring wear element.

32. The system of claim 30, wherein there is further provided a data correlation arrangement for correlating the electrical force signal against the rotatory information in said electrical rotatory data signal.

33. The system of claim 32, wherein there is further provided a lubricant supply flow rate control arrangement.

34. The system of claim 33, wherein said lubricant supply flow rate control arrangement controls a lubricant supply flow rate to a predetermined flow rate within a range of approximately between 0.2 l/h and 500 ml/h.

35. The system of claim 33, wherein there is further provided a controllable lubricant drain for controlling an accumulation of the lubricant.

36. The system of claim 30, wherein there is further provided a temperature control arrangement for controlling the temperature of the cylinder wall wear element and the piston ring wear element.

37. The system of claim 36, wherein said temperature control arrangement comprises a thermocouple arrangement coupled thermally to the piston ring wear element.

38. The system of claim 30, wherein said linear actuator comprises a pneumatic cylinder/piston assembly.

39. The system of claim 38, wherein there is further provided an air regulator for controlling the linear force applied by said pneumatic cylinder/piston assembly.

40. The system of claim 38, wherein there is further provided a force gauge coupled to said pneumatic cylinder/piston assembly for monitoring the linear force applied by said pneumatic cylinder/piston assembly.

41. The system of claim 30, wherein there is further provided a balancing weight coupled to said crank coupling arrangement for balancing rotational inertia forces.

42. The system of claim 30, wherein there is further provided a rotatory inertial mass coupled to said crank coupling arrangement for reducing angular speed variations of said crank coupling arrangement.

43. The system of claim 30, wherein said second support arrangement comprises a two-point load transfer arrangement coupled to the piston ring wear element for enabling a frictional communication between the piston ring wear element and the cylinder wall wear element to be responsive to a resilience characteristic of the piston ring wear element.

44. The system of claim 30, wherein said second support arrangement is arranged to enable a circumferential displacement of the piston ring wear element with respect to the frictional communication with the cylinder wall wear element.

45. A method of collecting correlatable data responsive to a simulated friction environment between first and second wear elements in frictional communication with one another, the method comprising the steps of:

driving the first wear element along a predetermined path of reciprocation;

driving a dynamic counter-reciprocating arrangement;

supporting the second wear element;

driving a second support arrangement that supports the second wear element, in a direction transverse to the predetermined path of reciprocation;

permitting the second wear element to tilt with respect to the first wear element in response to said step of driving a second support arrangement;

producing an electrical force data signal responsive to a force applied by the second wear element to the first wear element in response to said step of third driving; and producing an electrical rotatory data signal containing position information in response to said step of first driving.

46. The method of claim 45, wherein said step of producing an electrical force data signal comprises the step of producing an electrical normal force data signal responsive to a normal force applied by the second wear element in a normal direction against the first wear element.

47. The method of claim 45, wherein there is provided the further step of third producing an electrical friction force data signal responsive to a friction force between the second wear element and the first wear element in response to said step of driving the second support arrangement.

48. The method of claim 45, wherein there are provided the further steps of:

calculating an instantaneous coefficient of friction for the frictional communication between the first and second wear elements; and correlating the instantaneous coefficient of friction to the electrical rotatory data signal.

49. The method of claim 48, wherein said step of calculating an instantaneous coefficient of friction comprises the further steps of:

determining a friction force of the simulated friction environment between the first and the second wear elements; and calculating a ratio of the friction force of the simulated friction environment and the data in the electrical force data signal.

50. The method of claim 48, wherein there is further provided the step of repeating said steps of calculating and correlating at each of a plurality of respective rates at which said step of first driving is performed.

51. The method of claim 48, wherein there is further provided the step of delivering a predetermined quantity of lubricant to the region of frictional communication between the first and second wear elements.

52. The method of claim 51, wherein there is further provided the step of repeating said steps of calculating and correlating at each of a plurality of respective predetermined quantities of lubricant during said step of first driving.

53. The method of claim 52, wherein the predetermined quantities of lubricant correspond to respective predetermined rates of lubricant delivery to the region of frictional communication between the first and second wear elements.

54. The method of claim 53, wherein there is further provided the step of timing the electrical rotatory data signal for producing a speed signal.

55. The method of claim 45, wherein said steps of driving the first wear element and driving a dynamic counter-reciprocating arrangement comprise the further step of controlling second harmonic inertial forces.

56. A method of collecting correlatable data responsive to a simulated friction environment between first and second wear elements in frictional communication with one another, the method comprising the steps of:

driving the first wear element along a predetermined path of reciprocation;

driving a dynamic counter-reciprocating arrangement;

supporting the second wear element in predetermined spatial relation to the first wear element;

driving a second support arrangement that supports the second wear element, in a direction transverse to the predetermined path of reciprocation;

permitting The second wear element to tilt with respect to the first wear element in response to said step of driving a second support arrangement; and measuring a roughness characteristic of at least a selected one of said first and second wear elements.

57. The method of claim 56, wherein said step of measuring comprises the step of forming an optical photo-microscopic evaluation of said selected one of said first and second wear elements, the optical photo-microscopic evaluation containing information relating to a distribution of the roughness characteristic over a predetermined surface area of said selected one of said first and second wear elements.

58. The method of claim 57, wherein said step of measuring comprises the step of correlating a roughness characteristic of said selected one of said first and second wear elements to a distance therealong.

59. The method of claim 56, wherein there is further provided the step of measuring the speed of performance of said step of driving the first wear element.

60. The method of claim 56, wherein there is further provided the step of measuring a friction force during said step of driving the second support arrangement.

61. The method of claim 56, wherein there is further provided the step of measuring a normal force during said step of driving the second support arrangement.

* * * * *